United States Patent [19]
Lee et al.

[11] Patent Number: 6,150,457
[45] Date of Patent: Nov. 21, 2000

[54] ONE-COMPONENT THERMOSET COATING COMPOSITIONS

[75] Inventors: Sze-Ming Lee, Moon Township; Douglas A. Wicks, Mt. Lebanon, both of Pa.; Eberhard Koenig, Leverkusen, Germany; Carol L. Kinney, Eighty Four; Karen M. Henderson, Coraopolis, both of Pa.

[73] Assignees: Bayer Corporation, Pittsburgh, Pa.; Bayer Aktiengesellscaft, Leverkusen, Germany

[21] Appl. No.: 09/197,912

[22] Filed: Nov. 23, 1998

[51] Int. Cl.$^7$ .............................. C08L 61/24; C08L 61/28; C08L 77/00; C08L 79/08; C08L 83/00; C08L 83/04; C07C 281/02; C07C 281/06

[52] U.S. Cl. .......................... 524/845; 524/502; 524/507; 524/555; 524/588; 524/589; 524/590; 524/591; 524/600; 524/606; 524/608; 524/612; 524/831; 524/838; 524/843; 524/869; 525/123; 525/124; 525/329.4; 525/504; 525/509; 525/474; 525/418; 525/454; 525/456; 528/28; 528/45; 528/256; 528/259; 528/262; 528/263; 528/407; 528/422; 528/332; 528/335; 528/350; 560/25; 560/26; 560/115; 560/157; 560/158; 560/159; 560/160; 560/166; 564/35; 428/423.1; 428/447; 428/473.5; 428/474.4; 428/500; 428/524; 540/202; 544/67; 544/68; 544/222; 548/951; 548/952; 548/953

[58] Field of Search .................................. 528/28.45, 332, 528/256, 259, 335, 262, 263, 350, 407, 422; 524/502, 507, 555, 590, 591, 588, 600, 606, 608, 612, 831, 838, 843, 845, 869, 589; 560/25, 26, 115, 157, 158, 159, 160, 166; 564/35; 525/123, 124, 329.4, 504, 509, 474, 418, 454, 456; 428/423.1, 447, 473.5, 474.4, 500, 524; 540/202; 544/67, 68, 222; 548/951, 952, 953

[56] References Cited

U.S. PATENT DOCUMENTS

| | | | |
|---|---|---|---|
| 3,513,125 | 5/1970 | Kehr | 528/121 |
| 3,585,200 | 6/1971 | Sheppard et al. | 544/388 |
| 3,594,231 | 7/1971 | Kraebel | 429/188 |
| 3,755,288 | 8/1973 | Sheppard et al. | 534/816 |
| 3,755,443 | 8/1973 | Sheppard et al. | 564/37 |
| 3,993,609 | 11/1976 | Kamens et al. | 521/88 |
| 4,029,615 | 6/1977 | Kamens et al. | 521/50 |
| 4,308,184 | 12/1981 | Thoma et al. | 524/512 |
| 4,767,552 | 8/1988 | Sowerby | 252/46.3 |
| 4,883,907 | 11/1989 | Simonek et al. | 560/24 |
| 5,055,545 | 10/1991 | Lawson | 528/61 |
| 5,631,339 | 5/1997 | Faler et al. | 528/45 |

Primary Examiner—Rabon Sergent
Attorney, Agent, or Firm—Joseph C. Gil; Thomas W. Roy

[57] ABSTRACT

The present invention relates to compounds containing modified hydrazide groups and corresponding to formula I

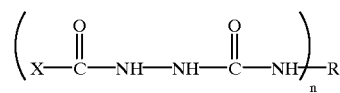

(I)

wherein

R represents the residue obtained by removing the isocyanate groups from a monomeric polyisocyanate, a polyisocyanate adduct or an NCO prepolymer, X represents OR' or NHR' and R' represents a group which is inert to isocyanate groups under the conditions used to form the compound of formula I and n has a value of 2 to 6.

The present invention also relates to one-component, thermoset coating compositions containing the compounds of formula I and a cross-linking component that is reactive with these compounds. Finally, the present invention relates coatings, sealants and adhesives prepared from these thermoset compositions.

12 Claims, No Drawings

ONE-COMPONENT THERMOSET COATING COMPOSITIONS

BACKGROUND OF THE INVENTION

1. Field of the Invention

The present invention relates to polyisocyanate-based resins containing modified hydrazide groups, to one-component, thermoset compositions containing these resins and a cross-linking component and to their use for the production of coatings, sealants and adhesives.

2. Description of the Prior Art

One-component polyurethane coating compositions derived from blocked polyisocyanates and polyols are an important class of materials for applications such as automotive OEM coatings. These one-component compositions are used because of the difficulties encountered when using two-component coating compositions in industrial applications. In the two-component compositions the polyisocyanates are not blocked, which results in several disadvantages. The two-component compositions must be accurately mixed or the properties of the resulting coatings can be substantially affected. In addition, after the components are mixed they have a limited pot life since the components continue to react until an unusable solid is obtained.

These disadvantages are not present in one-component coating compositions containing polyols and polyisocyanates blocked with reversible, monofunctional blocking agents for isocyanate groups. However, there are also disadvantages with one-component coating compositions, which are primarily caused by the volatilization of the blocking agent. The release of the blocking agent can cause blistering and yellowing in thick films and oven fouling. In addition, the blocking agents are considered to be volatile organic compounds (VOC's) in the same manner as organic solvents. Therefore, certain coating compositions may not satisfy environmental regulations solely due to the presence of blocking agents.

It is an object of the present invention to overcome the known disadvantages of one-component coating compositions caused by the release of blocking agents during cure without affecting the advantages of these coating compositions when compared to two-component coating compositions. It is an additional object of the present invention to be able to obtain coatings that possess chemical stability, including acid etch resistance, which is comparable to that obtained from coatings prepared using blocked polyisocyanates as the crosslinking agent.

These objects can be achieved with the one-component compositions according to the present invention. These compositions do not require blocking agents and, thus, do not release blocking agents. When the coating compositions according to the invention are cured, the only compounds released are water or monoalcohols, which are much less toxic than conventional blocking agents.

SUMMARY OF THE INVENTION

The present invention relates to compounds containing modified hydrazide groups and corresponding to formula I

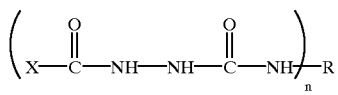

wherein
R represents the residue obtained by removing the isocyanate groups from a monomeric polyisocyanate, a polyisocyanate adduct or an NCO prepolymer,
X represents OR' or NHR' and
R' represents a group which is inert to isocyanate groups under the conditions used to form the compound of formula I and
n has a value of 2 to 6.

The present invention also relates to one-component, thermoset compositions containing the compounds of formula I and a cross-linking component that is reactive with these compounds. Finally, the present invention relates coatings, sealants and adhesives prepared from these thermoset compositions.

DETAILED DESCRIPTION OF THE INVENTION

The compounds containing modified hydrazide groups according to the present invention may be prepared by several different methods. For example, a polyisocyanate can be reacted with an excess of hydrazine to form a compound containing terminal $NH-NH_2$ groups, which can subsequently be reacted with an ester of chloroformic acid (X=OR) or a monoisocyanate (X=NHR) to form the compounds of formula I.

The compounds of formula I can also be prepared by reacting a polyisocyanate, $R-(NCO)_n$, with a compound corresponding to formula II

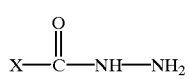

wherein X and R' are as previously defined.
In formulas I and II
X represents OR' or NHR', preferably OR', and
R' represents a group which is inert to isocyanate groups under the conditions used to form the compound of formula I, preferably an alkyl, cycloalkyl, araliphatic or aromatic group containing 1 to 20, preferably 1 to 10 carbon atoms, which may optionally be substituted by heteroatoms to form ether or ester groups.

When X represents OR', examples of R' include methyl, ethyl, propyl, butyl, hexyl, octyl, phenyl, cyclohexyl and benzyl. Most preferably, R' is an alkyl group having 1 to 4 carbon atoms. When X represents NHR, R' is most preferably an alkyl group containing at least 4 carbon atoms.

Compounds corresponding to formula II wherein X represents NHR' can be prepared by reacting hydrazine with an organic monoisocyanate in a molar ratio of 1:1. In order to increase the amount of product corresponding to formula II, it is also possible to use an excess amount of hydrazine and to remove the excess, e.g., by precipitation, distillation or extraction. However, this is generally not necessary since the selectivity to form the monoadduct is very high.

Examples of suitable polyisocyanates which may be used as the polyisocyanate component to prepare the compounds of formula I include monomeric polyisocyanates, polyisocyanate adducts and NCO prepolymers having an average functionality of 1.5 to 6, preferably 1.8 to 6, more preferably 2 to 6 and most preferably 2 to 4.

Suitable monomeric diisocyanates may be represented by the formula $$R(NCO)_2$$

in which R represents an organic group obtained by removing the isocyanate groups from an organic diisocyanate having a molecular weight of about 112 to 1,000, preferably about 140 to 400. Diisocyanates preferred for the process according to the invention are those represented by the above formula in which R represents a divalent aliphatic hydrocarbon group having 4 to 40, preferably 4 to 18 carbon atoms, a divalent cycloaliphatic hydrocarbon group having 5 to 15 carbon atoms, a divalent araliphatic hydrocarbon group having 7 to 15 carbon atoms or a divalent aromatic hydrocarbon group having 6 to 15 carbon atoms.

Examples of suitable organic diisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-iso-cyanatocyclohexyl)-methane, 2,4'-dicyclohexyl-methane diisocyanate, 1,3- and 1,4-bis-(isocyanatomethyl)-cyclohexane, bis-(4-isocyanato-3-methyl-cyclohexyl)-methane, α,α,α',α'-tetramethyl-1,3- and/or -1,4-xylylene diisocyanate, 1-isocyanato-1-methyl-4(3)-isocyanatomethyl cyclohexane, 2,4- and/or 2,6-hexahydrotoluylene diisocyanate, 1,3- and/or 1,4-phenylene diisocyanate, 2,4- and/or 2,6-toluylene diisocyanate, 2,4- and/or 4,4'-diphenyl-methane diisocyanate, 1,5-diisocyanato naphthalene and mixtures thereof.

Polyisocyanates containing 3 or more isocyanate groups such as 4-isocyanatomethyl-1,8-octamethylene diisocyanate and aromatic polyisocyanates such as 4,4',4"-triphenylmethane diisocyanate and polyphenyl polymethylene polyisocyanates obtained by phosgenating aniline/formaldehyde condensates may also be used.

Preferred organic diisocyanates include 1,6-hexamethylene diisocyanate, 1-isocyanato-3-isocyanatomethyl-3,5,5-trimethyl-cyclohexane (isophorone diisocyanate or IPDI), bis-(4-isocyanato-cyclohexyl)-methane, 1-isocyanato-1-methyl4(3)-isocyanatomethyl cyclohexane, 2,4- and/or 2,6-toluylene diisocyanate, and 2,4- and/or 4,4'-diphenyl-methane diisocyanate.

In accordance with the present invention the polyisocyanate component may be in the form of a polyisocyanate adduct. Suitable polyisocyanate adducts are those containing isocyanurate, uretdione, biuret, urethane, allophanate, iminooxadiazine dione, carbodiimide and/or oxadiazine-trione groups. The polyisocyanates adducts have an average functionality of 2 to 6 and an NCO content of 5 to 30% by weight and include:

1) Isocyanurate group-containing polyisocyanates which may be prepared as set forth in DE-PS 2,616,416, EP-OS 3,765, EP-OS 10,589, EP-OS 47,452, U.S. Pat. No. 4,288,586 and U.S. Pat. No. 4,324,879. The isocyanato-isocyanurates generally have an average NCO functionality of 3 to 3.5 and an NCO content of 5 to 30%, preferably 10 to 25% and most preferably 15 to 25% by weight.

2) Uretdione diisocyanates which may be prepared by oligomerizing a portion of the isocyanate groups of a diisocyanate in the presence of a suitable catalyst, e.g., a trialkyl phosphine catalyst, and which may be used in admixture with other aliphatic and/or cycloaliphatic polyisocyanates, particularly the isocyanurate group-containing polyisocyanates set forth under (1) above.

3) Biuret group-containing polyisocyanates which may be prepared according to the processes disclosed in U.S. Pat. Nos. 3,124,605; 3,358,010; 3,644,490; 3,862,973; 3,903,126; 3,903,127; 4,051,165; 4,147,714; or 4,220,749 by using co-reactants such as water, tertiary alcohols, primary and secondary monoamines, and primary and/or secondary diamines. These polyisocyanates preferably have an NCO content of 18 to 22% by weight and an average NCO functionality of 3 to 3.5.

4) Urethane group-containing polyisocyanates which may be prepared in accordance with the process disclosed in U.S. Pat. No. 3,183,112 by reacting excess quantities of polyisocyanates, preferably diisocyanates, with low molecular weight glycols and polyols having molecular weights of less than 400, such as trimethylol propane, glycerine, 1,2-dihydroxy propane and mixtures thereof. The urethane group-containing polyisocyanates have a most preferred NCO content of 12 to 20% by weight and an (average) NCO functionality of 2.5 to 3.

5) Allophanate group-containing polyisocyanates which may be prepared according to the processes disclosed in U.S. Pat. Nos. 3,769,318, 4,160,080 and 4,177,342, and copending application, U.S. Ser. No. 08/432,285. The allophanate group-containing polyisocyanates have a most preferred NCO content of 12 to 21% by weight and an (average) NCO functionality of 2 to 4.5. Preferred catalysts for the preparation of these polyisocyanates include organic tin(II) salts such as tin(II) octoate.

6) Isocyanurate and allophanate group-containing polyisocyanates which may be prepared in accordance with the processes set forth in U.S. Pat. Nos. 5,124,427, 5,208,334, 5,235,018 and 5,444,146, the disclosures of which are herein incorporated by reference, preferably polyisocyanates containing these groups in a ratio of monoisocyanurate groups to monoallophanate groups of about 10:1 to 1:10, preferably about 5:1 to 1:7.

7) Iminooxadiazine dione and optionally isocyanurate group-containing polyisocyanates which may be prepared in the presence of special fluorine-containing catalysts as described in DE-A 19611849. These polyisocyanates generally have an average NCO functionality of 3 to 3.5 and an NCO content of 5 to 30%, preferably 10 to 25% and most preferably 15 to 25% by weight.

8) Carbodiimide group-containing polyisocyanates which may be prepared by oligomerizing di- or polyisocyanates in the presence of known carbodiimidization catalysts as described in DE-PS 1,092,007, U.S. Pat. No. 3,152,162 and DE-OS 2,504,400, 2,537,685 and 2,552,350.

9) Polyisocyanates containing oxadiazinetrione groups and containing the reaction product of two moles of a diisocyanate and one mole of carbon dioxide.

Preferred polyisocyanate adducts are the polyisocyanates containing isocyanurate groups, uretdione, biuret groups, iminooxadiazine dione and/or allophanate groups.

The NCO prepolymers, which may also be used as the polyisocyanate component to prepare the compounds of formula I, are prepared from the previously described monomeric polyisocyanates or polyisocyanate adducts, preferably monomeric diisocyanates, and organic compounds containing at least two isocyanate-reactive groups, preferably at least two hydroxy groups.

These organic compounds include high molecular weight compounds having molecular weights of 400 to about 6,000, preferably 800 to about 3,000, and optionally low molecular weight compounds with molecular weights below 400. The molecular weights are number average molecular weights ($M_n$) and are determined by end group analysis (OH and/or NH number). Products obtained by reacting polyisocyanates exclusively with low molecular weight compounds are polyisocyanates adducts containing urethane groups and are not considered to be NCO prepolymers.

Examples of the high molecular weight compounds are polyester polyols, polyether polyols, polyhydroxy polycarbonates, polyhydroxy polyacetals, polyhydroxy polyacrylates, polyhydroxy polyester amides and polyhydroxy polythioethers. The polyester polyols, polyether polyols and polyhydroxy polycarbonates are preferred, while the polyester polyols and polyhydroxy polycarbonates are more preferred.

Examples of suitable high molecular weight polyhydroxyl compounds include polyester polyols prepared from low molecular weight alcohols and polybasic carboxylic acids such as adipic acid, sebacic acid, phthalic acid, isophthalic acid, tetrahydrophthalic acid, hexahydrophthalic acid, maleic acid, the anhydrides of these acids and mixtures of these acids and/or acid anhydrides. Polylactones having hydroxyl groups, particularly poly-ε-caprolactone, are also suitable for producing the prepolymers.

Also suitable for preparing the NCO prepolymers are polyether polyols, which may be obtained in known manner by the alkoxylation of suitable starter molecules. Examples of suitable starter molecules include polyols, water, organic polyamines having at least two N—H bonds and mixtures thereof. Suitable alkylene oxides for the alkoxylation reaction are preferably ethylene oxide and/or propylene oxide, which may be used in sequence or in admixture.

Other suitable polyols include polycarbonates having hydroxyl groups, which may be produced by the reaction of diols with phosgene or diaryl carbonates such as diphenyl carbonate.

Further details concerning the low molecular weight compounds and the starting materials and methods for preparing the high molecular weight polyhydroxy compounds are disclosed in U.S. Pat. No. 4,701,480, herein incorporated by reference.

Other examples include the known high molecular weight amine-functional compounds, which may be prepared by converting the terminal hydroxy groups of the polyols previously described to amino groups, and the high molecular weight polyaspartates and polyaldimines disclosed in U.S. Pat. Nos. 5,243,012 and 5,466,771, respectively, herein incorporated by reference. A particular advantage for the use of polyaspartates to prepare the isocyanate addition products is that during the subsequent curing of these products the urea groups react to form thermally stable hydantoin groups.

The NCO prepolymers generally have an isocyanate content of 0.4 to 20% by weight, preferably 0.4 to 15% by weight and more preferably 0.5 to 10.0% by weight. The NCO prepolymers are prepared in known manner by the reaction of the above mentioned starting materials at a temperature of 40 to 120° C., preferably 50 to 100° C. and at an NCO/OH (or NH) equivalent ratio of about 1.3:1 to 20:1 preferably about 1.4:1 to 10:1. If chain extension via urethane groups is desired during the preparation of the isocyanate prepolymers, an NCO/OH equivalent ratio of 1.3:1 to 2:1 is selected. If chain extension is not desired, an excess of diisocyanate is preferably used, corresponding to an NCO/OH equivalent ratio of 4:1 to 20:1, preferably 5:1 to 10:1. The excess diisocyanate (and any volatile solvent used during the preparation) may optionally be removed by thin layer distillation when the reaction is completed. In accordance with the present invention NCO prepolymers also include NCO semi-prepolymers which contain unreacted starting polyisocyanates in addition to the urethane group-containing prepolymers.

The compounds containing modified hydrazide groups may be prepared by reacting the polyisocyanate with the compound corresponding to formula II at a temperature of 20 to 150° C., preferably 50 to 100° C. The amount of the compounds corresponding to formula II should be sufficient to react with all or substantially all (i.e., up to 90 equivalent %), preferably all, of the isocyanate groups of the polyisocyanate.

To prepare the one-component, thermoset compositions the compounds of formula I are blended with a compound that is reactive with the modified hydrazide functional groups. These reactive groups include active methylol or methylalkoxy groups on aminoplast crosslinking agents or on other compounds such as phenol/formaldehyde adducts, siloxane or silane groups and anhydride groups.

Examples include melamine formaldehyde resins (including monomeric or polymeric melamine resins and partially or fully alkylated melamine resins), urea resins (e.g., methylol ureas such as urea formaldehyde resins and alkyoxy ureas such as butylated urea formaldehyde resins), N-methylol acrylamide emulsions, isobutoxy methyl acrylamide emulsions, polyanhydrides (e.g., polysuccinic anhydride), and siloxanes or silanes (e.g., dimethyldimethoxy silane). Preferred are aminoplast resins such as melamine formaldehyde resins or urea formaldehyde resins.

To control the crosslink density of the final product, it is possible to react off one or more of the amino nitrogens or hydroxy groups. For example, alkylated melamine/formaldehyde or urea/formaldehyde resins can be reacted with a compound corresponding to formula III

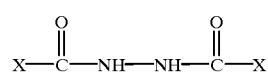

(III)

wherein X and R' are as defined above.

In the one-component, thermoset compositions according to the invention the compounds corresponding to formula I and the coreactants should preferably be present in an amount sufficient to provide an equivalent ratio of modified hydrazide groups to the groups that are reactive with the modified hydrazide groups of 2:1 to 1:6, more preferably 1.5:1 to 1:3, most preferably 1.2:1 to 1:2.5. When aminoplast resins, especially melamine resins, are used, they may be present in an amount of 10 to 70%, based on weight of the reactive components. This amount is higher than the above equivalent ratios, since these resins may also undergo self-crosslinking.

When aminoplast compounds, especially monomeric melamines are used as the co-reactant for the compounds of formula I, strong acid catalysts are preferred. These catalysts are well known and include p-toluenesulfonic acid, dinonylnaphthalene disulfonic acid, dodecylbenzenesulfonic acid, phenyl acid phosphate, monobutyl maleate, butyl phosphate and hydroxy phosphate ester. Other catalysts that may be useful include Lewis acids, zinc salts and tin salts.

The one-component compositions may contain the organic solvents known from melamine chemistry. These solvents may be present in an amount of up to 95%, preferably up to 80%, based on the total weight of the thermoset composition. Alcohols may be added to improve shelf stability.

It is also possible in accordance with the subject application to use water as the solvent. If the thermoset compositions are dispersed in water, the reactants preferably have a hydrophilic character, which may be obtained in known manner by incorporating ionic and/or non-ionic hydrophilic groups into the reactants and/or by the use of external emulsifiers.

The one-component, thermoset compositions of the present invention are suitable for preparing coatings, adhesives or sealants. Depending upon the particular application the compositions may also contain known additives, such as leveling agents, wetting agents, flow control agents, anti-skinning agents, antifoaming agents, fillers (such as silica, aluminum silicates and high-boiling waxes), viscosity regulators, plasticizers, pigments, dyes, UV absorbers and stabilizers against thermal and oxidative degradation.

The one-component compositions may be applied to any heat resistant substrates, preferably metals, glass and ceramics, and more preferably metals. They may be applied by standard methods, such as spray coating, spread coating, flood coating, casting, dip coating, roll coating. The coating compositions may be clear or pigmented.

The one-component, thermoset compositions are cured at elevated temperatures of 80 to 250° C., preferably 100 to 230° C. and more preferably 100 to 160° C., for a period of 5 to 60 minutes, preferably 10 to 50 minutes and more preferably 20 to 40 minutes.

The invention is further illustrated, but is not intended to be limited by the following examples in which all parts and percentages are by weight unless otherwise specified.

EXAMPLES

The following starting materials were used in the examples:

Polyol 1

A polyester polyol having an OH equivalent weight of 400, an OH content of 4.25% and a functionality of about 3.1 and prepared from 34.6 parts 1,6-hexane diol, 9.8 parts trimethylol propane, 30.43 parts isophthalic acid, 5.4 parts phthalic acid anhydride and 10.7 parts adipic acid.

Polyol 2

A polyester polyol having a molecular weight of 840 and prepared from 1,6-hexane diol and adipic acid.

Polyisocyanate 1

An isocyanurate group-containing polyisocyanate prepared from 1,6-hexamethylene diisocyanate and having an isocyanate content of 21.6%, a content of monomeric diisocyanate of <0.2% and a viscosity at 20 C of 3000 mPa.s (available from Bayer Corporation as Desmodur N 3300).

Example 1

334 parts of isophorone diisocyanate and 223 parts of butyl acetate were charged into a 2 liter, round bottomed flask fitted with a condenser.

566 parts of polyol 2 was weighed into a 1 liter flask and dried under vacuum at 100° C. 377 parts of butyl acetate were then added. The solution was placed in a dropping funnel and added dropwise into the IPDI solution over a 2 hour period. The temperature was maintained at 70 to 80° C. After all the polyol was added, the mixture was heated at 80° C. for 6 hours. An NCO prepolymer was obtained which had an NCO content of 5.2%, based on solution.

423 parts of the NCO prepolymer (423 g) were stirred at 60° C. in a 1 liter, 3-neck round bottomed flask fitted with a condenser. 47 parts of ethyl carbazate followed 31 parts of butyl acetate (31 g) were subsequently added. The mixture was heated at 70° C. for 4 hours and then placed in an oven heated to 70° C. overnight. The resulting product had a solids content of 60%.

Example 2

236 parts of isophorone diisocyanate and 156 parts of propylene glycol monomethyl ether acetate (MPA) were charged into a 2 liter, round bottomed flask fitted with a condenser.

343 parts of Polyol 1 and 157 parts of Polyol 2 (157 g) were weighed into a 1 liter flask and dried under vacuum at 100° C. 269 parts of MPA were added to the polyol mixture. The resulting solution was placed into a dropping funnel and added dropwise to the IPDI solution over a 2 hour period. The temperature was maintained at 70 to 80° C. After all the polyol was added, the mixture was heated at 80° C. for 3 hours. An NCO prepolymer was obtained which had an NCO content of 4.1%, based on solution.

428 parts of the NCO prepolymer were stirred at 60° C. in a 1 liter, 3-neck round bottomed flask fitted with a condenser. 43 parts of ethyl carbazate (43 g) followed by 29 parts of MPA were subsequently added. The mixture was heated at 70° C. for 4 hours and then placed in an oven heated to 70° C. overnight. The resulting product had a solids content of 60%.

Example 3

293 parts of isophorone diisocyanate, 57 parts of polyisocyanate 1 and 234 parts of MPA were charged into a 2 liter, round bottomed flask fitted with a condenser.

540 parts of polyol 1 and 117 parts of polyol 2 were weighed into a 1 liter flask and dried under vacuum at 100° C. 258 parts of MPA were then added to the mixture. The solution was placed in a dropping funnel and added dropwise into the mixture of isocyanates over a 2 hour period. The temperature was maintained at 70 to 80° C. After all the polyol was added, the mixture was heated at 80° C. for 6 h. An NCO prepolymer was obtained which had an NCO content of 4.2%, based on solution.

424 parts of the NCO prepolymer (424 g) was stirred at 60° C. in a 1 liter, 3-neck round bottomed flask fitted with a condenser. 46 parts of ethyl carbazate followed by 31 parts of MPA were subsequently added. The mixture was heated at 70° C. for 4 hours and then placed in an oven heated to 70° C. overnight. The resulting product had a solids content of 60%.

Example 4

A coating composition was prepared from 10 g of the product of Example 1, 0.6 g of methoxylated hexamethylol melamine (Resimene 747, Solutia) and 0.3 g of a 10% solution of p-toluenesulfonic acid in isopropanol. The composition was drawn down onto a rolled steel panel with a 5 mil drawdown bar and baked at 130° C. for 30 min. The resulting coating was clear and insoluble in acetone.

Example 5

A coating composition was prepared from 8.3 g of the product of Example 2, 0.6 g of methoxylated hexamethylol melamine (Resimene 747, Solutia) and 0.3 g of a 10% solution of p-toluenesulfonic acid in isopropanol. The composition was drawn down onto a rolled steel panel with a 5 mil drawdown bar and baked at 130° C. for 30 min. The resulting coating was clear and insoluble in acetone.

Example 6

A coating composition was prepared from 8.5 g of the product of Example 3, 0.6 g of methoxylated hexamethylol melamine (Resimene 747, Solutia) and 0.3 g of a 10% solution of p-toluenesulfonic acid in isopropanol. The composition was drawn down onto a rolled steel panel with a 5 mil drawdown bar and baked at 130° C. for 30 min. The resulting coating was clear and insoluble in acetone.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A compound containing modified hydrazide groups and corresponding to formula I

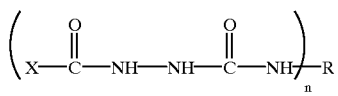

(I)

wherein

R represents the residue obtained by removing the isocyanate groups from a polyisocyanate adduct or an NCO prepolymer, X represents OR' or NHR' and R' represents a group which is inert to isocyanate groups under the conditions used to form the compound of formula I and n has a value of 2 to 6.

2. The compound of claim 1 wherein

R' represents an alkyl group containing 1 to 10 carbon atoms.

3. The compound of claim 1 wherein

X represents OR'.

4. The compound of claim 2 wherein

X represents OR'.

5. The compound of claim 1 wherein

R represents the residue obtained by removing the isocyanate groups from an NCO prepolymer.

6. The compound of claim 2 wherein

R represents the residue obtained by removing the isocyanate groups from an NCO prepolymer.

7. The compound of claim 3 wherein

R represents the residue obtained by removing the isocyanate groups from an NCO prepolymer.

8. The compound of claim 4 wherein

R represents the residue obtained by removing the isocyanate groups from an NCO prepolymer.

9. A one-component, thermoset composition comprising a compound containing modified hydrazide groups and corresponding to formula I

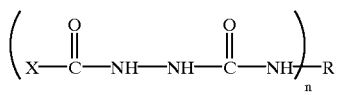

(I)

wherein

R represents the residue obtained by removing the isocyanate groups from a monomeric polyisocyanate, a polyisocyanate adduct or an NCO prepolymer, X represents OR' or NHR' and R' represents a group which is inert to isocyanate groups under the conditions used to form the compound of formula I and n has a value of 2 to 6, and a melamine formaldehyde resin, a urea resin, an N-methylol acrylamide emulsion, an isobutoxy methyl acrylamide emulsion, a polyanhydride, a siloxane or a silane.

10. The composition of claim 9 which comprises said compound corresponding to formula I, an acid catalyst and a melamine formaldehyde resin or a urea resin.

11. A heat resistant substrate coated with the thermoset composition of claim 9.

12. A heat resistant substrate coated with the thermoset composition of claim 10.

* * * * *